(12) United States Patent
Ikemura et al.

(10) Patent No.: US 8,835,675 B2
(45) Date of Patent: Sep. 16, 2014

(54) POLYMERIZABLE PHOSPHONIC ACID DERIVATIVE AND ADHESIVE COMPOSITION COMPRISING THE SAME

(75) Inventors: Kunio Ikemura, Kyoto (JP); Yoshiyuki Jogetsu, Kyoto (JP); So Ito, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 1588 days.

(21) Appl. No.: 11/949,972

(22) Filed: Dec. 4, 2007

(65) Prior Publication Data
US 2009/0048426 A1 Feb. 19, 2009

(30) Foreign Application Priority Data
Aug. 13, 2007 (JP) ................. 2007-210984

(51) Int. Cl.
*C07F 9/38* (2006.01)
*C09J 4/00* (2006.01)
*C09J 143/02* (2006.01)

(52) U.S. Cl.
CPC ............. *C07F 9/3808* (2013.01); *C09J 4/00* (2013.01); *C09J 143/02* (2013.01)
USPC ............. 562/11; 522/114; 522/115; 522/116; 522/137; 522/139

(58) Field of Classification Search
CPC .......... C08F 8/40; C08F 20/06; C08J 2385/02
USPC ........... 523/118; 528/399; 522/114, 115, 116, 522/137, 139; 562/11
See application file for complete search history.

(56) References Cited

U.S. PATENT DOCUMENTS

| 7,614,879 B2 * | 11/2009 | Nemoto et al. ............. 433/226 |
| 2003/0167968 A1 * | 9/2003 | Erdmann et al. ............. 106/35 |
| 2006/0135719 A1 * | 6/2006 | Moszner et al. ........... 526/303.1 |

FOREIGN PATENT DOCUMENTS

| JP | 2004-501940 | 1/2004 |
| JP | 2008-94862 | 4/2008 |

* cited by examiner

*Primary Examiner* — Sudhakar Katakam
*Assistant Examiner* — Pancham Bakshi
(74) *Attorney, Agent, or Firm* — Novak Druce Connolly Bove + Quigg LLP

(57) ABSTRACT

The present invention is directed to compounds and adhesives finding special utility in dental applications. Compounds of formulae:

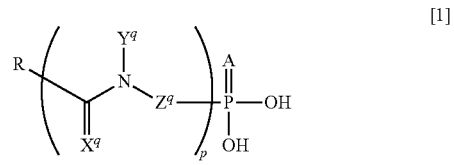

[1]

are of special interest, wherein:
R represents a polymerizable group of the structure

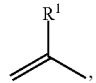

wherein $R^1$ represents a hydrogen atom or methyl group;
A represents an oxygen atom or a sulfur atom;
$X^q$s represent independently an oxygen atom or a sulfur atom;
$Y^q$s represent independently hydrogen atom;
$Z^q$s may independently represent $D-R^2$ where D represents a single carbon atom and $R^2$ represents phenyl;
p is an integer from 1 to 10; and
q is an integer from 1 to p.

11 Claims, No Drawings

POLYMERIZABLE PHOSPHONIC ACID DERIVATIVE AND ADHESIVE COMPOSITION COMPRISING THE SAME

CROSS-REFERENCED TO RELATED APPLICATIONS TO WHICH BENEFIT IS CLAIMED

This application claims benefit under 35 U.S.C. §119(a) and (b)(1) of foreign application number JP 2007-210984, filed Aug. 13, 2007, in Japan.

TECHNICAL FIELD

The present invention relates to a polymerizable phosphonic acid derivative which is a compound having intramolecularly a polymerizable group and a phosphonic acid group or a salt thereof. The present invention also relates to an adhesive composition comprising the above polymerizable phosphonic acid derivative such as an adhesive or a primer, which can show a strong adhesive strength in adhering tooth substances and dental restorative and prosthetic materials.

BACKGROUND

In a dental clinic, caries treatments are carried out by eliminating caries parts from tooth to form cavities, and by filling composite resin after applying a dental adhesive to the cavities. However, when adhesion properties of these materials are insufficient, there are problems such as dental pulp stimulation, secondary caries, detachment of composite resin and the like.

Conventionally, as a dental adhesive, a one liquid-type self-etching primer, a one-liquid type one-step bonding agent and the like which comprise essentially adhesive monomers such as a (meth)acrylate monomer having intramolecularly an acidic group have been proposed and produced. However, there are problems such as hydrolysis of ester bonds of the (meth)acrylate monomers in a strong acidic solution, deterioration of adhesion properties by hydrolysis at an adhesion interface between an adhesive and tooth substances and the like.

Recently, many manners on (meth)acrylamide monomers having an acidic group for excluding unstable factors in adhesion properties are disclosed.

Macromolecule Chemistry Physics vol. 200, pp. 1062-1067 (1999) reports that a phosphonic acid group-containing monomer having no ester bond prevents adhesion deterioration caused by hydrolysis and improves shelf lives of products.

JP 2003-89613A and Journal of Dental Research, Vo. 83. Special Issue No. #2661 report that a self-etching primer comprising N-methacryloyl-ω-aminoalkylphosphonic acid and N-methacryloyl glycin prevents adhesion properties from deterioration caused by hydrolysis.

However, while N-methacryloyl-ω-aminoalkylphosphonic acid, for example, N-methacryloylaminoethylphosphonic acid is excellent in hydrolysis stability when used in an aqueous primer, it has a defect not to solve into hydrophobic resin.

Recently, many adhesive monomers are reported which is characterized by so-called anti-hydrolysis stability. Such adhesive monomers are disclosed in JP 2006-176511A, JP 2006-176522A, JP 2006-199695A, JP 2006-514114A, and JP 2006-520344A and the like.

Among them, since the compounds disclosed in JP 2006-176511A, JP 2006-176522A and JP 2006-520344A have intramolecularly a phosphate group, they have a risk in which their C—O—P bonds are hydrolyzed.

Regarding the compounds disclosed in JP 2006-199695A and JP 2006-514114A, anti-hydrolysis stability can be expected but solubility in water and hydrophobic resin is problematic.

As discussed above, although a variety of adhesive monomers have been proposed to date in order to solve the problem that adhesion properties deteriorate due to reduction of shelf lives of products caused by hydrolysis in aqueous self-etching primers and dental one-liquid type one-step bonding agents, they are not satisfactory.

DISCLOSURE OF THE INVENTION

Problem to be Solved by the Invention

To date, a variety of adhesive monomers relating to a (meth)acrylamide monomer having an acidic group have been proposed in order to exclude unstable factors in adhesion properties such as hydrolysis of ester bonds of the (meth) acrylate monomers, hydrolysis at an adhesion interface between an adhesive and tooth substances and the like in a strong acidic solution. However, they are not satisfactory to solve the above problems.

Means for Solving the Problem

The present inventors have first developed a polymerizable phosphonic acid derivative which is a compound having intramolecularly a polymerizable group and a phosphonic acid group and a salt thereof, and confirmed that an adhesive composition comprising the polymerizable phosphonic acid derivative showed strong adhesion strength in adhering tooth substances and dental prosthetic materials and stability to hydrolysis in an acidic composition. Consequently, the present inventors have completed the present invention.

Effect of the Invention

As discussed above, since the polymerizable phosphonic acid derivative which is a compound having intramolecularly a polymerizable group and a phosphonic acid group or a salt thereof, and the adhesive composition comprising the polymerizable phosphonic acid derivative may solve the conventional problem so as to ensure treatment of caries and preservation of teeth of patients while maintaining a shelf life and adhesion properties of an adhesive composition. Thus, the present invention is worthy and greatly contributes to a dental treatment field.

Since the adhesive composition comprising an aminophosphonic acid derivative of the present invention which has intramolecularly one N-(meth)acryloyl group maintains its shelf life and adhesion properties, it may be used not only in a dental field but also in an orthopedic field and in a general industry field relating to adhesive, paint, lacquer and the like.

BEST MODE FOR CARRYING OUT THE INVENTION

That is, the present invention provides a polymerizable phosphonic acid derivative which is a compound having intramolecularly a polymerizable group and a phosphonic acid group and represented by the general formula [1]:

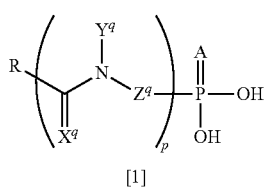

[1]

wherein
R represents a polymerizable group;
A represents an oxygen atom or a sulfur atom;
$X^q$s represent independently an oxygen atom or a sulfur atom;
$Y^q$s represent independently the same or different organic group;
$Z^q$s may be independently the same or different from each other and, a part of the $Z^q$s optionally selected or all of the $Z^q$s represent organic groups having a substituent which is an organic group other than a polymerizable group and a phosphonic acid group;
p is an integer from 1 to 10;
q is an integer from 1 to p;
when p is 1,
q is 1;
$X^1$ represents an oxygen atom or a sulfur atom;
$Y^1$ represents an organic group;
$Z^1$ represents an organic group having one or more of substituents which are organic groups other than an acidic group and a polymerizable group, or a salt thereof.

Further, the present invention provides a polymerizable phosphonic acid derivative which is a compound having intramolecularly a polymerizable group and a phosphonic acid group and represented by the general formula [2] rather than the general formula [1]:

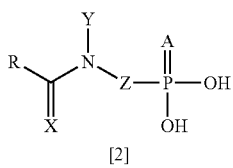

[2]

wherein
R represents a polymerizable group;
A represents an oxygen atom or a sulfur atom;
X represents an oxygen atom or a sulfur atom;
Y represents a hydrogen atom or an organic group;
Z represents an organic group having one or more of substituents other than a polymerizable group and a phosphonic acid group, and wherein
Y and Z may form a cyclic organic group together with a nitrogen atom to which they attach, or a salt thereof.

Even further, the present invention provides a polymerizable phosphonic acid derivative which is a compound having intramolecularly a polymerizable group and a phosphonic acid group and represented by the general formula [3] rather than the general formulas [1] and [2]:

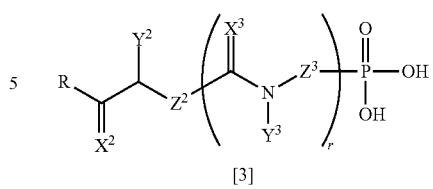

[3]

wherein
R represents a polymerizable group;
$X^2$ and $X^3$ represent independently an oxygen atom or a sulfur atom;
$Y^2$ and $Y^3$ represent independently a hydrogen atom or an organic group;
both or either of $Z^2$ and $Z^3$ represents an organic group having one or more of substituents other than a polymerizable group and a phosphonic acid group; and wherein
$Y^2$ and $Z^2$ or $Y^3$ and $Z^3$ may form a cyclic organic group; and
r represents 0 or 1, or a salt thereof.

Still further, the present invention especially provides a polymerizable phosphonic acid derivative which is a compound represented by the general formula [4] rather than the general formulas [1] to [3]:

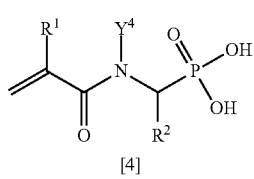

[4]

wherein
$R^1$ represents a hydrogen atom or a methyl group;
$R^2$ represents an organic group other than a polymerizable group and a phosphonic acid group;
$Y^4$ represents a hydrogen atom or an organic group, or a salt thereof.

Yet further, the present invention especially provides a polymerizable phosphonic acid derivative which is a compound having intramolecularly a polymerizable group and a phosphonic acid group and represented by the general formula [5] rather than the general formulas [1] to [3]:

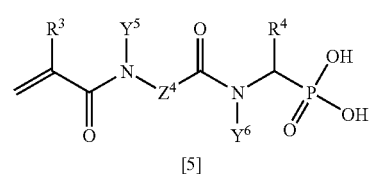

[5]

wherein
$R^3$ represents a hydrogen atom or a methyl group;
$R^4$ represents an organic group optionally having a substituent other than an acidic group and a polymerizable group;
$Y^5$ and $Y^6$ represent independently a hydrogen atom or an organic group;
$Z^4$ represents an organic group optionally having a substituent other than a polymerizable group or a phosphonic acid group; and wherein $Y^5$ and $Z^4$ or $Y^6$ and $Z^4$ may form a cyclic organic group, or a salt thereof.

Yet even further, the present invention provides a polymerizable phosphonic acid derivative in which the salt of the compound represented by any one of the general formulas [1] to [5] is a salt with a metal atom selected from a group consisting of alkali metals, alkaline earth metals, transition metals, Zn and Cd, or a salt with an amine.

The present invention provides a polymerizable phosphonic acid derivative which is a compound having intramolecularly a polymerizable group and a phosphonic acid group and represented by the general formula [6] rather than the general formulas [1] to [5]:

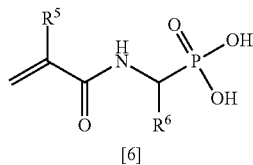

[Chemical Formula 6]

[6]

wherein $R^5$ represents a hydrogen atom or a methyl group;

$R^6$ represents an organic group other than a polymerizable group and a phosphonic acid group, or a salt of the phosphonic acid group with an alkali metal, an alkaline earth metal or an amine, and an adhesive composition comprising the polymerizable phosphonic acid derivative.

In the present invention, the polymerizable phosphonic acid derivative represented by the general formulas [1] to [6] may be
synthesized by any synthesis methods.

For example, the present compound represented by the general formula [6], in particular, an aminophosphonic acid derivative having intramolecularly an N-(meth)acryloyl group may be synthesized by forming an intermediate A, aminophosphonic acid represented by the general formula [7]:

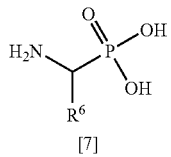

[Chemical Formula 7]

[7]

wherein $R^6$ is the same as defined in the general formula [6], by Oleksyszyn reaction or Kabachnik-Fields reaction and, then, by reacting with (meth)acrylate chloride by Schotten-Baumann reaction.

The intermediate A, aminophosphonic acid may be synthesized by Oleksyszyn reaction in which aldehyde, phosphorus trichloride and benzyl carbamate are reacted together.

The polymerizable phosphonic acid derivatives of the present invention, in particular, an aminophosphonic acid derivative having intramolecularly an N-(meth)acryloyl group may be synthesized by reacting the above aminophosphonic acid with (meth)acrylate chloride (Schotten-Baumann reaction).

The present aminophosphonic acid derivative having intramolecularly an N-(meth)acryloyl group may also be synthesized by Kabachnik-Fields reaction and Schotten-Baumann reaction.

For example, diethyl phosphite, substituted aldehyde and ammonium acetate are reacted in one pot by Kabachnik-Fields reaction in the presence of 3 Å molecular sieves to synthesize diethyl aminophosphonate, and this is hydrolyzed to form an intermediate aminophosphonic acid. Further, by reacting the intermediate with (meth)acrylate chloride, the present compound (1) N-(meth)acryloylaminophosphonic acid may be synthesized.

As the present aminophosphonic acid derivative having intramolecularly an N-(meth)acryloyl group, for example, the present compound (1) N-(meth)acryloylaminophosphonic acid may be synthesized by reacting diethyl phosphite, substituted aldehyde and ammonium acetate in one-pot by Kabachnik-Fields reaction in the presence of 3 Å molecular sieves to synthesize diethyl aminophosphonate, reacting this with (meth)acrylate chloride by Schotten-Baumann reaction to synthesize diethyl N-(meth)acryloylaminophosphonate, and hydrolyzing this.

In addition, the present invention provides a polymerizable phosphonic acid derivative which is a compound having intramolecularly a polymerizable group and a phosphonic acid group and a salt thereof.

The present invention provides an adhesive composition comprising a radical polymerizable phosphonic acid derivative which is a compound having intramolecularly a polymerizable group and a phosphonic acid group or a salt thereof, and an adhesive composition comprising the radical polymerizable phosphonic acid derivative.

A compound represented by the general formula [8]:

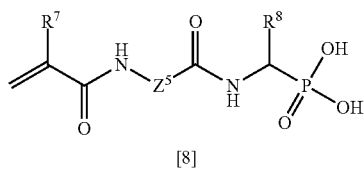

[Chemical Formula 8]

[8]

wherein $R^7$ represents a hydrogen atom, a methyl group, an alkyl group or an aromatic group;

$R^8$ is an organic group other than an acidic group and a polymerizable group, and represents an alkyl group, an alkoxy group or an aromatic group;

$Z^5$ represents an alkyl group optionally having a substituent, or a methylene group or an alkyl group having a carbon number of 1 to 13, or an aromatic group, or a salt of the phosphonic acid group with an alkali metal, an alkaline earth metal or an amine may be synthesized by any synthesis process.

In the general formula representing the polymerizable phosphonic acid derivative of the present invention, the term "organic group" means a hydrocarbon group (which may include optional elements other than carbon and hydrogen, such as oxygen, nitrogen, sulfur, phosphorus, or silicon) which is assorted into an aliphatic group, a cyclic group, and a combination of an aliphatic group and a cyclic group (e.g., alkaryl and aralkyl groups). In the present invention, this organic group is that does not inhibit formation of an etching agent for a hard tissue surface.

The term "cyclic group" means a closed-circular hydrocarbon group, and is assorted into an alicyclic group, an aromatic group, and a heterocyclic group. It is preferable that their polymerizable group is an ethylenic unsaturated group. More preferably, the ethylenic unsaturated group is a (meth)acrylate group, a (meth)acrylamide group or a vinyl group.

As one embodiment of processes for synthesizing the present compound represented by the general formula [8], for example, aminophosphonic acid is synthesized as Intermediate A by Oleksyszyn reaction or Kabachnik-Fields reaction similar to the compound represented by the general formula [8].

Further, (meth)acrylate chloride and aminoalkylcarbonic acid are reacted to synthesize N-(meth)acryloylaminoalkylcarbonic acid (Intermediate B).

The present compound represented by the general formula [8] may be synthesized by an amidation reaction of aminophosphonic acid (Intermediate A) and N-(meth)acryloylaminoalkylcarbonic acid (Intermediate B).

In the present invention, (meth)acryloyl includes both methacryloyl and acryloyl, for example, N-(meth)acryloyl-1-amino-1-benzylphosphonic acid includes N-methacryloyl-1-amino-1-benzylphosphonic acid and N-acryloyl-1-amino-1-benzylphosphonic acid.

As mentioned above, the present compound N-(meth)acryloylaminophosphonic acid includes all compounds synthesized by reacting aminophosphonic acid derivatives and (meth)acrylate chloride.

Such compounds includes, for example, N-(meth)acryloyl-1-amino-1-benzylphosphonic acid (N-methacryloyl-1-phenyl-1-aminophosphonic acid), N-methacryloyl-1-toluoyl-1-aminophosphonic acid, N-methacryloyl-1-methyl-1-aminophosphonic acid, N-methacryloyl-1-ethyl-1-aminophosphonic acid, N-methacryloyl-1-butyl-1-aminophosphonic acid, N-methacryloyl-1-isobutyl-1-aminophosphonic acid, N-methacryloyl-1-propyl-1-aminophosphonic acid, N-methacryloyl-1-isopropyl-1-aminophosphonic acid, N-methacryloyl-1-pentyl-1-aminophosphonic acid, N-methacryloyl-1-isopentyl-1-aminophosphonic acid, N-methacryloyl-1-hexyl-1-aminophosphonic acid, N-methacryloyl-1-decyl-1-aminophosphonic acid, and their salts with an alkali metal, an alkaline earth metal or an amine.

It is particularly preferable that the present polymerizable phosphonic acid derivative which is a compound having intramolecularly a polymerizable group and a phosphonic acid group or a salt thereof is N-(meth)acryloyl-1-amino-1-benzylphosphonic acid, N-methacryloyl-1-methyl-1-aminophosphonic acid, N-methacryloyl-1-ethyl-1-aminophosphonic acid, N-methacryloyl-1-butyl-1-aminophosphonic acid, 5-(N-methacryloyl)pentyl-1-aminomethylphosphonic acid, 6-(N-methacryloyl)hexyl-1-aminomethylphosphonic acid, 10-(N-methacryloyl)decyl-1-aminomethylphosphonic acid, 6-(N-methacryloyl)hexyl-1-aminopropylphosphonic acid, 6-(N-methacryloyl)hexyl-2-aminopropylphosphonic acid, 10-(N-methacryloyl)decyl-2-aminopropylphosphonic acid, and their salts with an alkali metal, an alkaline earth metal or an amine.

The present invention relates to an adhesive composition comprising a polymerizable phosphonic acid derivative which is a compound having intramolecularly a polymerizable group and a phosphonic acid group and represented by any one of the general formulas [1] to [6] and [8], or a salt thereof.

In this text, the present adhesive composition includes an adhesive which is a composition showing adhesion properties and a primer which is a composition promoting adhesion properties of an adhesive.

In the present invention, an "adhesive" includes a dental bonding agent capable of promoting adhesion properties of a dental composite resin to enamel or dentin, a resin cement or a bonding agent improving an adhesion property to metal, a resin cement or a bonding agent promoting an adhesion property to dental ceramic materials or dental porcelain such as alumina and zirconia, and a self-adhesive composite resin comprising filler.

In the present invention, a "primer" includes a self-etching primer capable of improving adhesion properties to enamel or dentin by using a dental composite resin and a dental bonding agent, or a resin cement or a glass-ionomer cement, an adhesive metal primer improving an adhesion property to metals, a ceramic primer promoting an adhesion property to dental ceramic materials or dental porcelain such as alumina and zirconia.

The present invention provides an adhesive composition further comprising a polymerizable monomer other than the polymerizable phosphonic acid derivative which is a compound having intramolecularly a polymerizable group and a phosphonic acid group and represented by any one of the general formulas [1] to [6] and [8], or its salt.

In addition, the present invention provides an adhesive composition comprising (a) the polymerizable phosphonic acid derivative which is a compound having intramolecularly a polymerizable group and a phosphonic acid group and represented by any one of the general formulas [1] to [6] and [8], or a salt thereof, (b) a polymerizable monomer having an acidic group other than the polymerizable phosphonic acid derivative which is a compound having intramolecularly a polymerizable group and a phosphonic acid group and represented by any one of the general formulas [1] to [6] and [8], or a salt thereof, (c) a polymerizable monomer having no acidic group, (d) a polymerization initiator, and (e) water.

In the present invention, the polymerizable monomer having an acidic group other than the polymerizable phosphonic acid derivative which is a compound having intramolecularly a polymerizable group and a phosphonic acid group and represented by any one of the general formulas [1] to [6] and [8] or a salt thereof may be selected to use from monomers conventionally used as a dental adhesive monomer, in particular, radical polymerizable monomers having intramolecularly one or more of, for example, phosphoryl group such as a phosphate group, a phosphonic acid group, a diphosphate group; carboxyl groups and carboxylic anhydride groups; sulfonate groups, and a polymerizable group such as a (meth)acryloyl group and an N-(meth)acryloylamide group and the like, and salts of these radical polymerizable monomers having an acidic group with an alkali metal, an alkaline earth metal or an amine.

In the present invention, for example, methyl(meth)acrylate includes both methylmethacrylate and methylacrylate.

As a phosphonic acid group-containing radical polymerizable monomer, examples include 3-(meth)acryloxypropyl-3-phosphonopropionate, 3-(meth)acryloxypropylphosphonoacetate, 4-(meth)acryloxybutyl-3-phosphonopropionate, 4-(meth)acryloxybutylphosphonoacetate, 5-(meth)acryloxypentyl-3-phosphonopropionate, 5-(meth)acryloxypentylphosphonoacetate, 6-(meth)acryloxyhexyl-3-phosphonopropionate, 6-(meth)acryloxyhexylphosphonoacetate, bis[2-(meth)acryloxyethyl]hydrogenphosphate, 2-(meth)acryloyloxyethyldihydrogenphosphate, 3-(meth)acryloyloxypropyldihydrogenphosphate, 4-(meth)acryloyloxybutyldihydrogenphosphate, 5-(meth)acryloyloxypentyldihydrogenphosphate, 6-(meth)acryloyloxyhexyldihydrogenphosphate, N-(meth)acryloyl-ω-aminopropylphosphonic acid, and their salts with an alkali metal, an alkaline earth metal or an amine.

In the present invention, as a radical polymerizable monomer having intramolecularly a carboxyl group or a carboxylic anhydride group, examples include methacrylic acid, 4-(meth)acryloxyethyltrimellitic acid, 4-(meth)acryloyloxyethoxycarbonylphthalic acid, 4-(meth)acryloyloxybutyloxycarbonylphthalic acid, 4-(meth)acryloyloxyhexyloxycarbonylphthalic acid, 4-(meth)acryloyloxyoctyloxycarbonylphthalic acid, 4-(meth)acryloyloxydecyloxycarbonylphthalic acid, and anhydrides thereof, 2-(meth)acryloyloxyethylmaleic acid, 5-(meth)acryloylaminopentylcarboxylic acid, 6-(meth)acryloyloxy-1,1-hexanedicarboxylic acid, 7-(meth)acryloyloxy-1,1-heptanedicarboxylic acid, 8-(meth)acryloyloxy-1,1-octanedicarboxylic acid, 10-(meth)acryloyloxy-1,1-decanedicarboxylic acid, 11-(meth)acryloyloxy-1,1-undecanedicarboxylic acid, N-(meth)acryloylamino acids such as N-(meth)acryloylalanine, N-(meth)acryloylglycine, N-(meth)acryloylaspartic acid and the like, and their salts with an alkali metal, an alkaline earth metal or an amine.

In the present invention, as a radical polymerizable monomer having intramolecularly a sulfonate group, examples include styrenesulfonic acid, 2-sulfoethyl(meth)acrylate, 6-sulfohexyl(meth)acrylate, 10-sulfodecyl(meth)acrylate, 2-(meth)acrylamide-2-methylpropanesulfonic acid, and their salts with an alkali metal, an alkaline earth metal or an amine.

These radical polymerizable monomers having intramolecularly an acidic group may be used alone or appropriately in combination, it is preferable to use 6-(meth)acryloxyhexyl-3-phosphonoacetate, 6-(meth)acryloxyhexyl-3-phosphonopropionate, 10-(meth)acryloxydecylhydrogenphosphate, 4-(meth)acryloxyethyltrimellitic acid, 4-(meth)acryloxyethyltrimellitic anhydride and the like.

One or more of these radical polymerizable monomers having intramolecularly an acidic group may be optionally selected to use. The amount of these radical polymerizable monomers having intramolecularly an acidic group to be added is 1 to 80 weight %, preferably 3 to 60 weight %, and more preferably 5 to 30 weights with respect to the total amount of the adhesive composition of the present invention. When the amount is less than 1 weight % or more than 80 weight %, adhesion properties deteriorate.

Polymerizable monomers having no acidic group which may be used to the present invention are aliphatic and aromatic monofunctional or multifunctional radical polymerizable monomers and may be selected to use from monomers, oligomers and prepolymers having a radical polymerizable unsaturated double bond used in a dental field and a general industry field. In addition, polymerizable monomers having intramolecularly a sulfur atom, polymerizable monomers having intramolecularly a fluoroalkyl group, and compounds containing a functional group with a fluoride ion-releasability may also be used. One or more of these polymerizable monomers having no acidic group may be optionally selected to use.

Specific embodiments for these polymerizable monomers having no acidic group include ethyleneglycol di(meth)acrylate, triethyleneglycol di(meth)acrylate, hexamethyleneglycol di(meth)acrylate, 2,2-bis{4-(meth)acryloxypropoxyphenyl}propane; bisphenol A-diglycidyl (meth)acrylate, di(meth)acryloxyethyl-2,2,2-trimethylhexamethylenediurethane.

The water used in the present invention is medically acceptable water, and preferably purified water, distilled water and ion-exchanged water.

In the present invention, one or more of polymerization initiators may be optionally selected to use from, for example, peroxides, α-diketons, (bis)acylphosphone oxides, coumalin compounds, and thioxanthone derivatives and the like. Polymerization promoters may be further used. In order to achieve excellent hardening properties without depending on light sources used in commercial dental photopolymerization irradiator such as halogen lamps, LEDs, Xenon lamps and the like, a plurality of polymerization promoters may be selected to use together with these polymerization initiators.

It is preferable that one or more of the peroxides are optionally selected from benzoyl peroxide, 4,4'-dichlorobenzoyl peroxide, and tert-butylperoxymalleic acid. It is preferable that the α-diketons are DL-camphorquinon or benzil. It is preferable that the (bis)acylphosphine oxides are 2,4,6-trimethylbenzoyl methoxyphenylphosphine oxide, or bis(2,4,6-trimethylbenzoyl)acylphosphine oxide. It is preferable that the coumalin compounds are 3,3'-carbonylbis(7-diethylaminocoumalin) or 3,3'-carbonylbis(7-dibutylaminocoumalin). It is preferable that the thioxanthone derivatives are 2-chlorothioxanthen-9-one.

In addition, as a photopolymerization initiator, sodium 2,4,6-trimethylbenzoylphenylphosphineoxide and 2-hydroxy-3-(3,4-dimethyl-9H-thioxanthen-2-yloxy)-N,N,N-trimethyl-1-propaneaminium chloride, which are water soluble photopolymerization initiators, may also be used.

The polymerization promoter used in the present invention is preferably amines such as N,N-di(2-hydroxyethyl)-p-toluidine, ethyl 4-N,N-dimethylaminobenzoate; barbituric acids such as 5-butylbarbituric acid, 1,3,5-trimethylbarbituric acid, 1-cyclohexyl-5-ethylbarbituric acid, 1-benzyl-5-phenylbarbituric acid; an organic tin compound such as di-N-octyl-tin dilaulate and di-N-butyl-tin dilaulate; and a trihalomethyl substituted-1,3,5-triazine compound such as 2,4,6-tris (trichloromethyl)-1,3,5-triazine, 2-(p-methoxyphenyl)-4-bis (trichloromethyl)-1,3,5-triazine.

An organic solvent may be added to the present invention. Acetone and ethanol are particularly preferable.

Filler may be added to the present invention. Ultrafine particle filler, fluorine sustained-releasing filler, polymer and silica filler are preferable filler.

Filler may be properly used in the adhesive composition of the present invention in order to adjust mechanical strength, handling, coating property, fluidity. Filler usable generally in dentistry may be used. Ultrafine filler, fluoride ion-releasing filler, polymers and silica filler are particularly preferred.

As a polymerization inhibitor contained in the adhesive composition of the present invention in order to prevent the composition from gelling and to stabilize a shelf life, examples include hydroquinone, hydroquinone monomethyl ether, butylate hydroxytoluene and the like, and hydroquinone monomethyl ether and butylate hydroxytoluene are suitable.

As discussed above, the present invention provides an adhesive composition comprising a component (a) polymerizable phosphonic acid derivative of the present invention, a component (b) polymerizable monomer other than the polymerizable phosphonic acid derivative of the present invention, a component (c) polymerizable monomer having no acidic group, a component (d) polymerization initiator, and a component (e) water, wherein the amount of each components are the following: 0.01 to 70 weight % for the component (a), 0.01 to 70 weight % for the component (b), 0.01 to 60 weight % for the component (c), and 0.01 to 30 weight % for the component (d), 0.1 to 40 weight % for preferably the component (a), 0.1 to 40 weight % for the component (b), 0.1 to 40 weight % for the component (c) and 0.1 to 10 weight % for the component (d), more preferably 0.1 to 30 weight % for the component (a), 0.1 to 30 weight % for the component (b), 0.1 to 30 weight % for the component (c) and 0.1 to 5 weight % for the component (d) when the total amount of the components (a) to (d) is assumed to be 100 weight %. In addition, the amount of the component (e) water to be added is 0.1 to 99.5 weight %, preferably 5 to 80 weight %, more preferably 10 to 60 weight % with respect to 100 weight % of the total amount of the adhesive composition of the present invention.

Accordingly, if required, a water insoluble acidic group-containing radical polymerizable monomer, a radical polymerizable monomer having intramolecularly no acidic group, a polymerization initiator, filler, an organic solvent, a modifier, a thickening agent, dye, pigment may be properly selected to add in the adhesive composition of the present invention. As these agents, a gents used in a dental field and a general industry field may be used.

The adhesive composition according to the present invention in one embodiment may be used together with a dental composite resin, a low-viscous composite resin, a resin cement, a resin modified glass ionomer cement, a fissure sealant, an adhesive for orthodontics, a tooth surface coating, an opaque material and the like as a one-liquid type self-etching primer or a one-liquid type one-step bonding agent.

EXAMPLES

The present invention will be specifically explained by referring to Examples and Comparative examples below. It should be understood that the present invention never be limited within the following examples.

Example 1

Synthesis of
1-[(N-methacryloyl)aminobenzyl]-phosphonic acid
(MABP)

(1A) Synthesis of 1-(aminobenzyl)-phosphonic acid
(ABP)

To a mixed solution of benzyl carbamate (27.5 g, 182 mmol), phosphorus trichloride (25.0 g, 182 mmol) and glacial acetic acid (55 g), freshly distilled benzaldehyde (29.0 g, 273 mmol) was added dropwise at room temperature over 20 minutes. This mixed solution was reacted by refluxing for 2 hours. Hydrochloric acid at normality of 4 (50 ml) was added and the solution was heated to reflux overnight. After cooling at room temperature, and discarding an organic layer with a separating funnel, an aqueous layer was refluxed for 30 minutes with an activated carbon. After separating the activated carbon by filtration, the filtrate was concentrated. Slurry was made by adding methanol to the residue, and it was neutralized by adding propylene oxide dropwise with cooling at 4 to 10° C. The obtained solid was recrystallized from a mixed solvent of water/methanol to obtain 25.5 g (136 mmol) of 1-(aminobenzyl)-phosphonic acid (ABP) as white crystals. It is presumed that since enantiomers exist, two types of methine protons derived from aldehyde were observed.

Yield: 75% m.p.: 280-282° C.

Nuclear magnetic resonance spectra ($^1$H NMR) (300 MHz, D$_2$O, ppm): δ 7.36-7.30 (m, 5H, Ph-H), 4.33, 4.28 (s×2, NH$_2$—C—H).

(1B) Synthesis of
1-[(N-methacryloyl)aminobenzyl]-phosphonic acid
(MABP)

Sodium hydroxide (14.1 g, 353 mmol) was added to distilled water (100 ml), 1-(aminobenzyl)-phosphonic acid (ABP) (20.0 g, 107 mmol) was solved into the mixed solution and, then, freshly distilled methacrylic chloride (13.4 g, 128 mmol) was added dropwise at an inner temperature of 14 to 16° C. over 20 minutes. This mixed solution was reacted at a room temperature of 18 to 21° C. for 2 hours and, then, the solution was made acidic by addition of hydrochloric acid, and the precipitated sodium chloride was separated by filtration. The filtrate was concentrated. These procedures were repeated several times until the salt did not precipitate. After concentration, the filtrate was dried by vacuuming at 35° C. to obtain 15.4 g (60 mmol) of 1-[(N-methacryloyl)aminobenzyl]-phosphonic acid (MABP) as white crystals. It is presumed that since enantiomers exist, two types of methine protons derived from amide and aldehyde were observed.

Yield: 57%

$^1$H NMR (500 MHz, DMSO-d$_6$, ppm): δ 8.23-8.19 (d×2, 1H, N—H), 7.51-7.19 (m, 5H, Ph-H), 5.79 (s, 1H, CH=C—), 5.39 (s, 1H, CH=C—), 5.30-5.19 (d×2, 1H, Ph-C—H), 1.87 (s, 3H, CH$_3$—).

Nuclear magnetic resonance spectra $^{13}$C NMR (75 MHz, DMSO-d$_6$, ppm): δ 167.6-167.5 (d, C=O), 139.5 (s, CH$_2$=C), 137.9-127.0 (m, C$_6$H$_5$), 120.3 (s, CH$_2$=C), 52.9-51.0 [d, NH—CH(C$_6$H$_5$)—P], 18.9 (s, CH$_3$—).

From the above analysis results, the product was confirmed as MABP.

Example 2

Synthesis of
1-[(N-methacryloyl)aminoethyl]-phosphonic acid
(MAEP)

(2A) Synthesis of 1-(aminoethyl)-phosphonic acid
(AEP)

To a mixed solution of benzyl carbamate (18.5 g, 123 mmol), phosphorus trichloride (18.5 g, 182 mmol) and glacial acetic acid (37 g), freshly distilled acetaldehyde (8.1 g, 184 mmol) was added dropwise at room temperature over 20 minutes. This mixed solution was reacted by refluxing for 2 hours. Hydrochloric acid at normality of 4 (50 ml) was added and the solution was heated to reflux overnight. After cooling at room temperature, and discarding an organic layer with a separating funnel, an aqueous layer was refluxed for 30 minutes with an activated carbon. After separating the activated carbon by filtration, the filtrate was concentrated. Slurry was made by adding methanol to the residue, and it was neutralized by adding propylene oxide dropwise with cooling at 4 to 10° C. The obtained solid was recrystallized from a mixed solvent of water/methanol to obtain 11.2 g (90 mmol) of 1-(aminoethyl)-phosphonic acid (ABP) as white crystals.

Yield: 73% m.p.: 271-273° C.

$^1$H NMR [300 MHz, D$_2$O, ppm]: δ 3.28-3.16 (t×2, 1H, NH$_2$—C—H), 1.33-1.24 (d×2, 3H, CH$_3$).

(2B) Synthesis of
1-[(N-methacryloyl)aminoethyl]-phosphonic acid
(MAEP)

Sodium hydroxide (10.6 g, 264 mmol) was added to distilled water (80 ml), 1-(aminoethyl)-phosphonic acid (10.0 g, 80 mmol) was solved into the mixed solution and, then, freshly distilled methacrylic chloride (10.0 g, 96 mmol) was added dropwise at an inner temperature of 14 to 16° C. over 20 minutes. This mixed solution was reacted at a room temperature of 18 to 21° C. for 2 hours and, then, the solution was made acidic by addition of hydrochloric acid, and the precipitated sodium chloride was separated by filtration. The filtrate was concentrated. These procedures were repeated several times until the salt did not precipitate. After concentration, the filtrate was dried by vacuuming at 35° C. to obtain 12.0 g (10.1 mmol) of 1-[(N-methacryloyl)aminoethyl]-phosphonic acid (MAEP) as white crystals. It is presumed that since enantiomers exist, two types of methine protons derived from amide and aldehyde were observed.

Yield: 78%

$^1$H NMR (500 MHz, DMSO-$d_6$, ppm): δ 7.62-7.59 (d, 1H, N—H), 5.64 (s, 1H, CH=C—), 5.32 (s, 1H, CH=C—), 4.20-4.05 (m×2, 1H, C—H), 1.84 (s, 3H, $CH_3$—), 1.28-1.17 (d×2, 3H, $CH_3$).

$^{13}$C NMR (75 MHz, DMSO-$d_6$, ppm): δ 167.1-167.0 (d, C=O), 139.8 (s, $CH_2$=C), 119.6 (s, $CH_2$=C), 43.3-41.3 [d, NH—CH($CH_3$)—P], 18.8 (s, $CH_2$=C—$CH_3$), 15.7 [d, NH—CH($CH_3$)—P].

From the above analysis results, the product was confirmed as MAEP.

Example 3

Synthesis of 1-[(N-methacryloyl)aminobutyl]-phosphonic acid (MABuP)

(3A) Synthesis of 1-(aminobutyl)-phosphonic acid (ABuP)

To a mixed solution of benzyl carbamate (27.5 g, 182 mmol), phosphorus trichloride (25.0 g, 182 mmol) and glacial acetic acid (55 g), freshly distilled butyl aldehyde (8.1 g, 184 mmol) was added dropwise at room temperature over 20 minutes. This mixed solution was reacted by refluxing for 2 hours. Hydrochloric acid at normality of 4 (50 ml) was added and the solution was heated to reflux overnight. After cooling at room temperature, and discarding an organic layer with a separating funnel, an aqueous layer was refluxed for 30 minutes with an activated carbon. After separating the activated carbon by filtration, the filtrate was concentrated. Slurry was made by adding methanol to the residue, and it was neutralized by adding propylene oxide dropwise with cooling at 4 to 10° C. The obtained solid was recrystallized from a mixed solvent of water/methanol to obtain 18.0 g (118 mmol) of 1-(aminobutyl)-phosphonic acid (ABuP) as white crystals.

Yield: 65% m.p.: 280-282° C.

$^1$H NMR (400 MHz, $D_2O$, ppm): δ 3.11-3.04 (t×2, 1H, $NH_2$—C—H), 1.76-1.21 (m, 4H, CH—$CH_2$—$CH_2$—$CH_3$), 0.79-0.75 (t, 3H, —$CH_3$)

(3B) Synthesis of 1-[(N-methacryloyl)aminobutyl]-phosphonic acid (MABuP)

Sodium hydroxide (12.9 g, 323 mmol) was added to distilled water (100 ml), 1-(aminobutyl)-phosphonic acid (15.0 g, 98 mmol) was solved into the mixed solution and, then, freshly distilled methacrylic chloride (12.3 g, 118 mmol) was added dropwise at an inner temperature of 14 to 16° C. over 20 minutes. This mixed solution was reacted at a room temperature of 18 to 21° C. for 2 hours and, then, the solution was made acidic by addition of hydrochloric acid, and the precipitated sodium chloride was separated by filtration. The filtrate was concentrated. These procedures were repeated several times until the salt did not precipitate. After concentration, the filtrate was dried by vacuuming at 35° C. to obtain 10.1 g (46 mmol) of 1-[(N-methacryloyl)aminobutyl]-phosphonic acid (MABuP) as white crystals. It is presumed that since enantiomers exist, two types of methine protons derived from amide and aldehyde were observed.

Yield: 47%

$^1$H NMR [400 MHz, DMSO-$d_6$, ppm]: δ 7.66-7.64 (d, 1H, N—H), 5.70 (s, 1H, CH=C—), 5.30 (s, 1H, CH=C—), 4.15-4.05 (m×2, 1H, C—H), 1.84 (s, 3H, —$CH_3$), 1.82-0.99 (m, 4H, CH—$CH_2$—$CH_2$—$CH_3$), 0.87-0.80 (t, 3H, —$CH_3$).

From the above analysis results, the product was confirmed as MABuP.

Example 4

Synthesis of 1-[(N-methacryloyl)aminoheptyl]-phosphonic acid (MHEP)

(4A) Synthesis of 1-(aminoheptyl)-phosphonic acid (AHP)

To a mixed solution of benzyl carbamate (27.5 g, 182 mmol), phosphorus trichloride (25.0 g, 182 mmol) and glacial acetic acid (55 g), freshly distilled heptyl aldehyde (31.2 g, 273 mmol) was added dropwise at room temperature over 30 minutes. This mixed solution was reacted by refluxing for 2 hours. Hydrochloric acid at normality of 4 (50 ml) was added and the solution was heated to reflux overnight. After cooling at room temperature, and discarding an organic layer with a separating funnel, an aqueous layer was refluxed for 30 minutes with an activated carbon. After separating the activated carbon by filtration, the filtrate was concentrated. Slurry was made by adding methanol to the residue, and it was neutralized by adding propylene oxide dropwise with cooling at 4 to 10° C. The obtained solid was recrystallized from a mixed solvent of water/methanol to obtain 16.6 g (85 mmol) of 1-(aminoheptyl)-phosphonic acid as white crystals.

Yield: 47%

$^1$H NMR [400 MHz, $D_2O$, ppm]: δ 3.21-3.01 (t×2, 1H, $NH_2$—C—H), 1.81-1.16 (m, 10H, CH—$CH_2$—$CH_2$—$CH_2$—$CH_2$—$CH_2$—$CH_3$), 0.76-0.71 (t, 3H, —$CH_3$).

(4B) Synthesis of [1-(N-methacryloyl)aminoheptyl]-phosphonic acid (MHEP)

Sodium hydroxide (10.1 g, 254 mmol) was added to distilled water (100 ml), 1-(aminoheptyl)-phosphonic acid (15.0 g, 77 mmol) was solved into the mixed solution and, then, freshly distilled methacrylic chloride (9.6 g, 92 mmol) was added dropwise at an inner temperature of 14 to 16° C. over 20 minutes. This mixed solution was reacted at a room temperature of 18 to 21° C. for 2 hours and, then, the solution was made acidic by addition of hydrochloric acid, the precipitated sodium chloride was separated by filtration. The filtrate was concentrated. These procedures were repeated several times until the salt did not precipitate. After concentration, the filtrate was dried by vacuuming at 35° C. to obtain 9.7 g (37 mmol) of 1-[(N-methacryloyl)aminoheptyl]phosphonic acid (MAHP) as white crystals. It is presumed that since enantiomers exist, two types of methine protons derived from amide and aldehyde were observed.

Yield: 48%

$^1$H NMR [400 MHz, DMSO-$d_6$, ppm]: δ 7.63-7.60 (d, 1H, N—H), 5.69 (s, 1H, CH=C—), 5.31 (s, 1H, CH=C—), 4.11-4.01 (m×2, 1H, C—H), 1.84 (s, 3H, —CH$_3$), 1.73-1.00 (m, 10H, CH—CH$_2$—CH$_2$—CH$_2$—CH$_2$—CH$_2$—CH$_3$), 0.87-0.81 (t, 3H, —CH$_3$).

From the above analysis results, the product was confirmed as MHEP.

Example 5

Measurement of Shear Adhesion Strength

In order to practice the primer comprising the composition of the present invention as a dental self-etching primer, primer A was prepared by mixing the compound of the present invention (MABP) (15 parts by weight), distilled water (50 parts by weight), and acetone (35 parts by weight).

Primer B was prepared by mixing the compound of the present invention (MABP) (20 parts by weight), distilled water (50 parts by weight), and acetone (30 parts by weight).

Primer C was prepared by mixing the compound of the present invention (MABP) (15 parts by weight), 4-methacryloxyethyltrimellitic acid (4-MET) (5 parts by weight), distilled water (50 parts by weight), and acetone (30 parts by weight).

Primer D was prepared by mixing the compound of the present invention (MABP) (15 parts by weight), distilled water (50 parts by weight), acetone (35 parts by weight), DL-camphorquinone (0.1 parts by weight), ethyl N,N-dimethylaminobenzoate (0.1 parts by weight).

These prepared primers were used in measurements of shearing adhesion strength between enamel of tooth and a composite resin.

Freshly extracted bovine incisor was used as a tooth substance as substituted for a human tooth. The dental pulp was removed by cutting off the tooth root and then it was embedded in epoxy resin. Enamel on a labial side of the same bovine tooth was ground with water resistant abrasion paper #600 under running water. The ground tooth surface was dried by compressed air free of oil. Areas to be adhered were defined by sticking a double-sided sticky tape with a 4 mm-diameter hole. Next, a primer was dropped on a small dish and it was applied to the defined areas to be adhered with a microbrush. After treatment of rubbing for 10 seconds, volatiles were evaporated by weakly blowing compressed air free of oil for 5 seconds. On the surface, a light-cured bonding agent "Fluorobond II" (manufactured by Shofu Inc.) was applied with a microbrush and the material was spread over the tooth surface, followed by light-irradiation for 10 seconds using a Shofu Grip Light II (manufactured by Shofu Inc.). After that, a plastic mold with 4 mm diameter and 2 mm height was fixed within the frame of the defined area to be adhered, a light-cured composite resin "Beautifil II" (manufactured by Shofu Inc.) was filled into the mold. After photocuring the composite resin by light-irradiation for 20 seconds using a Shofu Grip Light II, the mold was removed to form an adhesion specimen.

After immersing the adhesion specimen into distilled water at 37° C. for 24 hours, the specimen was mounted on a holder for measuring shear adhesion strength and its shear adhesion strength was measured using an Instron Universal tester (Instron 5567, manufactured by Instron Corp.) at a crosshead speed of 1 mm/min. and calculated average values for n=8.

Shear adhesion strengths between dental enamel and the composite resin for respective cases using each of the primers were excellent, that is, 20.3 MPa for Primer A, 24.7 MPa for Primer B, 22.5 MPa for Primer C, 23.4 MPa for Primer D.

From the above results, it is demonstrated that the adhesive composition of the present invention is applicable as a self-etching primer for a dental orthodontic adhesive in which adhesion to enamel is especially required.

Example 6

In order to practice the adhesive compositions comprising the compound of the present invention as a one-liquid type one-step dental bonding agent, a dental bonding agent was prepared by mixing the compound of the present invention (MABP) (20 parts by weight), 4-methacryloyloxyethyltrimellitic acid (4-MET) (12.2 parts by weight), bisphenol-A-diglycidyl methacrylate (Bis-GMA) (12.8 parts by weight), triethyleneglycol dimethacrylate (TEGDMA) (8.5 parts by weight), distilled water (24.0 parts by weight), acetone (14.3 parts by weight), DL-camphorquinone (0.6 parts by weight), ethyl N,N-dimethylaminobenzoate (0.4 parts by weight), fine particle filler R-972 (0.16 microns: DEGUSSA, Germany) (1.2 parts by weight) and methoxyhydroquinone (MeHQ) (2000 ppm).

Aging tests were carried out by standing a plastic black container including 5 g of the bonding agent according to Example 6 at 50° C. for 4 weeks. Shear adhesion strengths between the bonding agent and enamel or dentin before and after aging were measured at a crosshead speed of 1 mm/min. Average values for measured specimens n=10 (standard deviation) are shown in Table 1.

Comparative Example 1

A bonding agent of Comparative example 1 was prepared by mixing respective components according to Example 6 with only one exception that the compound of the present invention (MABP) (20 parts by weight) in Example 6 was replaced by 6-methacryloyloxyhexylphosphonoacetate (6-MHPA) which is a conventional methacrylate derivative having a phosphonic acid group. Shear adhesion strength measurements between dental enamel and the composite resin by using the prepared bonding agents were carried out according to the method for measuring adhesion strength in Example 5 with only one exception that "a primer was dropped on a small dish and it was applied to the defined areas to be adhered with a microbrush; after treatment of rubbing for 20 seconds, volatiles were evaporated by weakly blowing compressed air free of oil for 10 seconds" in the adhering process of Example 5.

Aging tests were carried out by standing a plastic black container including 5 g of the bonding agent according to Comparative example 1 at 50° C. for 4 weeks. Shear adhesion strengths between the bonding agent and enamel and dentin before and after aging were measured at a crosshead speed of 1 mm/min. Average values [n=10 (standard deviation)] for measured specimens are shown in Table 1.

TABLE 1

| | | Adhesive monomer | pH of the liquid | Shear adhesion strength (MPa) | |
|---|---|---|---|---|---|
| | | | | immediately after preparation | after 4 weeks standing at 50° C. |
| Example 6 | to enamel | MABP | pH 2.0 | 20.9 (3.4)[a] | 17.8 (5.5)[a] |
| | to dentin | MABP | pH 2.0 | 19.5 (6.3)[a] | 18.3 (3.4)[a] |
| Comparative | to enamel | 6-MHPA | pH 2.1 | 17.8 (5.6)[a] | 3.8 (1.7)[b] |
| Example 1 | to dentin | 6-MHPA | pH 2.1 | 18.2 (4.8)[a] | 8.2 (3.4)[b] |

Aging tests were carried out for bonding agents comprising water. As clearly demonstrated from the results in Table 1, although there is no significant difference (probability 0.05%) between bond strengths of the composition comprising the compound of the present invention and the composition comprising the conventional adhesive monomer 6-MHPA immediately after preparation, there were significant differences (p<0.05%) for the values after 4 weeks standing at 50° C. From the above results, it is demonstrated that compositions comprising the compound of the present invention (MABP) suppressed reduction of a shelf life caused by hydrolysis and maintained strong adhesion strength to tooth substances.

What we claimed is:

1. A polymerizable phosphonic acid derivative which is a compound represented by the general formula [1]:

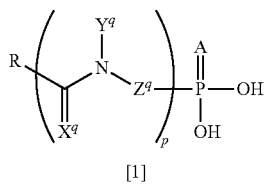

[1]

wherein

R represents a polymerizable group of the structure

wherein $R^1$ represents a hydrogen atom or methyl group;

A represents an oxygen atom or a sulfur atom;

$X^q$s represent independently an oxygen atom or a sulfur atom;

$Y^q$s represent independently hydrogen atom;

$Z^q$s may independently represent D-$R^2$ groups where D represents a single carbon atom and $R^2$ represents phenyl;

p is an integer from 1 to 10;

q is an integer from 1 to p;

when p is 1, q is 1;

$X^1$ represents an oxygen atom or a sulfur atom;

$Y^1$ represents hydrogen;

$Z^1$ represents methylbenzene, or a salt thereof.

2. The polymerizable phosphonic acid derivative, which is a compound represented by the general formula [4]:

[Chemical Formula 4]

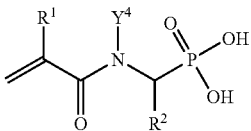

[4]

wherein $R^1$ represents a hydrogen atom or a methyl group;

$R^2$ represents a phenyl group;

$Y^4$ represents a hydrogen atom, or a salt thereof.

3. The polymerizable phosphonic acid derivative according to claim 1, which is a salt with a metal atom selected from a group consisting of alkali metals, alkaline earth metals, transition metals, Zn and Cd, or a salt with an amine.

4. The polymerizable phosphonic acid derivative, which is N-(meth)acryloyl-1-amino-1-benzylphosphonic acid, N-methacryloyl-1-methyl-1-aminophosphonic acid, or its salts with an alkali metal, an alkaline earth metal, transition metals, Zn or Cd or a salt with an amine.

5. The polymerizable phosphonic acid derivative according to claim 2, which is a salt with a metal atom selected from a group consisting of alkali metals, alkaline earth metals, transition metals, Zn and Cd, or a salt with an amine.

6. An adhesive composition comprising the polymerizable phosphonic acid derivative defined in claim 1.

7. An adhesive composition comprising the polymerizable phosphonic acid derivative defined in claim 2.

8. An adhesive composition comprising the polymerizable phosphonic acid derivative defined in claim 3.

9. An adhesive composition comprising the polymerizable phosphonic acid derivative defined in claim 4.

10. The polymerizable phosphonic acid derivative according to claim 4, which is a salt with a metal atom selected from a group consisting of alkali metals, alkaline each metals, or a salt with an amine.

11. An adhesive composition comprising the polymerizable phosphonic acid derivative defined in claim 10.

* * * * *